United States Patent [19]

Shimizu et al.

[11] Patent Number: 4,885,419

[45] Date of Patent: Dec. 5, 1989

[54] 1,2-DI(4-ISOBUTYLPHENYL)HYDROCARBON AND ITS PREPARATION AND USES AS INTERMEDIATE

[75] Inventors: Isoo Shimizu, Yokohama; Yasuo Matsumura, Yokohama; Yoshihisa Inomata, Kawasaki, all of Japan

[73] Assignee: Nippon Petrochemicals Company, Ltd., Japan

[21] Appl. No.: 190,506

[22] Filed: May 5, 1988

[30] Foreign Application Priority Data

May 6, 1987 [JP] Japan .................................. 62-110176
May 6, 1987 [JP] Japan .................................. 62-110177

[51] Int. Cl.$^4$ ...................... C07C 15/12; C07C 15/18
[52] U.S. Cl. ..................................................... 585/25
[58] Field of Search ............................................ 585/25

[56] References Cited

U.S. PATENT DOCUMENTS 4,493,943  1/1988  Sato et al. ............................. 585/25
4,694,100  9/1987  Shimizu et al. ...................... 562/419

FOREIGN PATENT DOCUMENTS 1222863  2/1971  United Kingdom .................. 585/25

OTHER PUBLICATIONS

Han, G. et al., "Hydrogenation Reactions of Some Spool–Shaped Acetylenes", *Journal of Organic Chemistry*, 1981, 46(23), 4695–4700 (with abstract).

*Primary Examiner*—Patrick P. Garvin
*Assistant Examiner*—George R. Foarson
*Attorney, Agent, or Firm*—Scully, Scott, Murphy & Presser

[57] ABSTRACT

Novel compounds of 1,2-di(isobutylphenyl)ethane and 1,2-di(isobutylphenyl)ethylene, method for producing the same and method for preparing 4-isobutylstyrene and α-(4-isobutylphenyl)propionic acid from any of these compounds. In the preparation of 4-isobutylstyrene from the former two compounds by cracking or disproportionation, the components in the resultant reaction mixture can be separated without difficulty, the formation of by-product isobutylbenzene can be avoided, and the remaining unreacted starting material can be reused for the same reaction without causing any adverse effect on a catalyst.

5 Claims, No Drawings

1,2-DI(4-ISOBUTYLPHENYL)HYDROCARBON AND ITS PREPARATION AND USES AS INTERMEDIATE

BACKGROUND OF THE INVENTION

(1) Field of the Invention

This invention relates to novel compounds of 1,2-di(4-isobutylphenyl)ethylene and 1,2-di(4-isobutylphenyl)ethane.

These novel compounds can be used as intermediate materials for preparing inexpensively and economically α-(4-isobutylphenyl)propionic acid (tradename: "Ibuprofen") which is useful as a medicine for the relief of fever, pain and inflammation.

Furthermore, the invention also relates to a method for producing ibuprofen through 4-isobutylstyrene from the above novel compounds.

(2) Description of the Prior Art

α-(4-isobutylphenyl)propionic acid is an excellent medicine because it is effectual in the relief of fever, pain and inflammation and it has little side effect. Therefore, various kinds of synthesis methods have been proposed. One of them, it is proposed to prepare the medicine from 4-isobutylstyrene through hydroformylation or Reppe process. More particularly, the method is proposed in, for example, British Patent No. 1,565,235 and U.S. Pat. No. 4,694,100.

This method using 4-isobutylstyrene is one of economically advantageous methods because 4-isobutylstyrene is a simple and stable substance and the hydroformylation and Reppe process do not require any expensive reagent.

As a method for producing alkylstyrenes, the catalytic cracking of 1,1-diarylethane is hitherto proposed. For instance, in the specification of the foregoing U.S. Pat. No. 4,694,100, a method for preparing 4-isobutylstyrene is disclosed in which method 1,1-di(4-isobutylphenyl)ethane is catalytically cracked. In the same patent specification, the method for preparing ibuprofen by hydroesterification or hydroformylation of 4-isobutylstyrene is also disclosed.

In this method, however, it cannot be avoided that an equimolar amount of isobutylbenzene is theoretically produced simultaneously with the formation of the aimed 4-isobutylstyrene. Accordingly, it has been necessary that this isobutylbenzene as a by-product is converted again into the starting material to be cracked.

Nevertheless, it has been found out that 4-isobutylstyrene can be obtained without the formation of the by-product, isobutylbenzene, by subjecting 1,2-di(4-isobutylphenyl)ethylene of the present invention to disproportionation with ethylene.

In addition, the above catalytic cracking of 1,1-di(isobutylphenyl)ethane has another disadvantage. That is, in the catalytic cracking as disclosed in the above references, not all of the starting material is cracked and it cannot be avoided that unreacted starting material remains in the reaction mixture. This is apparent from the fact that the purpose conversion rates in the method proposed above are from 40% to 60%.

In order to produce economically alkylstyrene by cracking, the reuse of the unreacted 1,1-di(substituted phenyl)ethane is inevitable. In other words, it is an inevitable condition for economizing the industrial practice of cracking reaction that the fraction mainly containing 1,1-di(substituted phenyl)ethane that is separated from a reaction mixture is used again for a cracking step.

The inventors of the present invention have made extensive investigation with regard to the preparation of alkylstyrene by cracking. As a result, it was found out that, in the conventional method for cracking 1,1-di(substituted phenyl)ethane, the properties of the fraction mainly containing 1,1-di(substituted phenyl)ethane is not suitable for use again in cracking, because ethylene components are contained; and that, when the new compound of 1,2-di(substituted phenyl)ethane is used as a material to be cracked, the formation of such ethylene components is not observed and any problem is not caused to occur even when the fraction containing unreacted material is used again. That is, in the cracking of 1,1-di(4-isobutylphenyl)ethane in the conventional art, ethylene components which are formed by dehydrogenation with a cracking catalyst are contained in the fraction of unreacted material as shown by the following chemical equation. In addition, these ethylene components are hardly separated by distillation because they have close boiling points. When the cracking of unreacted 1,1-di(4isobutylphenyl)ethane fraction containing ethylene components is carried out, the life of cracking catalyst is affected adversely.

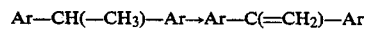

wherein Ar is an aryl group.

In connection with the new compound, 1,2-di(4-isobutylphenyl)ethane of the present invention, the formation of ethylene components can be avoided and the reuse of the fraction containing unreacted material does not affect adversely on the life of cracking catalyst, therefore, the efficient production of 4-isobutylstyrene could be first accomplished by this invention.

BRIEF SUMMARY OF THE INVENTION

It is, therefore, the object of the present invention to provide novel intermediate compounds for producing ibuprofen effectively and economically and a novel method for producing ibuprofen using the same.

That is, the present invention relates to 1,2-di(4-isobutylphenyl)hydrocarbons represented by the following general formula (I):

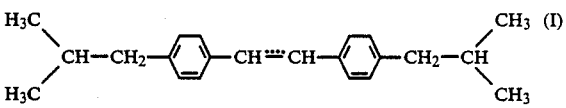

wherein the symbol represents a carbon-carbon single bond or double bond.

Namely, the compounds of the above formula are trans- and cis-1,2-di(4-isobutylphenyl)ethylene and 1,2-di(4-isobutylphenyl)ethane.

DETAILED DESCRIPTION OF THE INVENTION

The 1,2-di(4-isobutylphenyl)ethylene of the present invention can be prepared, for example, by the following method.

Isobutylbenzene is converted into di(4-isobutylphenyl)iodonium salt using potassium periodate in concentrated sulfuric acid and the obtained iodonium salt is reacted with ethylene in the presence of a palladium catalyst to obtain 1,2-di(4-isobutylphenyl)ethylene.

The halide of the above di(4-isobutylphenyl)iodonium salt can be prepared according to the methods described in the specifications of Japanese Laid-Open Patent Publication No. 53-101331, Japanese Patent Publication No. 57-53767, British Patent No. 1,114,950 and J. Amer. Chem. Soc., Vol. 81, 342 (1959). More particularly, isobutylbenzene and potassium periodate are mixed together with stirring in anhydrous acetic acid and a mixture of anhydrous acetic acid and concentrated sulfuric acid is then added dropwise to it. After that, precipitate is emerged out by adding saturated aqueous solution of ammonium chloride. The precipitate is then filtered off and to obtain di(4-isobutylphenyl)iodonium chloride. The outline of reaction is shown as follows:

wherein R is an aryl group.

In the above formula, the counter ion such as Cl$^-$ can be subjected to ion-exchange with any anions (inert to reaction) such as metal halide anions. Preferable counter ions are halogen ions such as chlorine ion and bromine ion.

Another reactant to be reacted with di(4-isobutylphenyl)iodonium salt is ethylene.

This reaction can be attained in a solvent by introducing ethylene gas in the presence of a catalyst of transition metal such as palladium and a basic substance such as potassium oxide. The reaction is represented as follows:

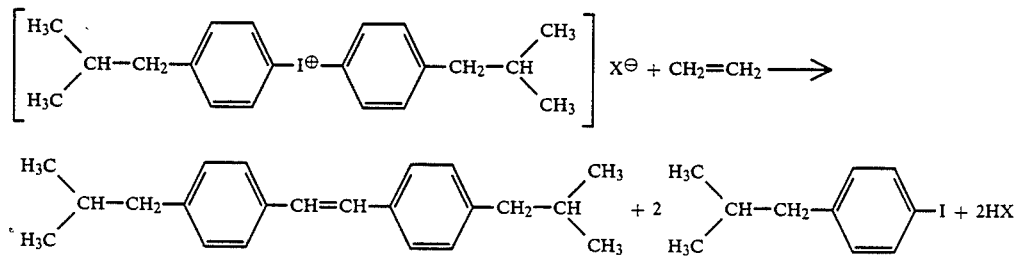

wherein X$^\ominus$ is a counter ion which is inert to the reaction.

The use quantity of a base may be the amount which is sufficient to neutralize the acid produced from the counter ion of di(4-isobutylphenyl)iodonium salt to be reacted. Accordingly, when the use quantity is less than a stoichiometric amount, the yield of 1,2-di(4-isobutylphenyl)ethylene is merely reduced. Therefore, the quantity of a base can be selected arbitrary. As far as a base is soluble in a reaction solvent, any kind of base can be employed. Exemplified as the bases are tertiary alkylamines such as triethylamine, tripropylamine, tributylamine, dimethylaniline and diethylaniline, alkali metal salts of lower fatty acids such as sodium acetate, potassium acetate and sodium formate, and carbonates or hydrogencarbonates of alkali metals such as sodium and potassium.

The catalysts used for the reaction with ethylene are transition metal catalysts of the group VIII elements of the periodic table, which are exemplified by palladium, rhodium, ruthenium, platinum, iridium and osmium. Among them, palladium catalysts are preferable. These transition metal catalysts are used in various forms, regardless of their oxidation numbers and the forms of complexes. In the case of palladium catalysts, palladium carried on alumina or activated carbon, divalent palladium compounds such as halogenated palladium such as palladium chloride, palladium oxide and the palladium salt of lower fatty acid such as palladium acetate, and complexes such as bis(dibenzylideneacetone)palladium. In the case of rhodium catalyst, the carbonyl complexes can also be used.

As the solvents used for the reaction may be those which dissolves di(4-isobutylphenyl)iodonium salt, even a little, and which are inert to the reaction. For example, lower alcohols such as methanol and ethanol, ketones such as acetone and methyl ethyl ketone, ethers such as dimethoxyethane and dioxane, and other polar solvents such as dimethylformamide, dimethyl sulfoxide, acetonitrile and tetrahydrofuran, can be properly selected. Incidentally, in the case that a used base acts also as a solvent, it is not necessary to use another solvent.

The reaction time of 0.5 to 10 hours is generally sufficient. After the reaction, the reaction mixture is sufficiently washed with water and cooled to obtain the crystal of 1,2-di(4-isobutylphenyl)ethylene. The precipitated crystal is then filtered off and refined by recrystallization with methanol to obtain 1,2-di(4-isobutylphenyl)ethylene.

The olefinic unsaturated bonds of the thus obtained 1,2-di(4-isobutylphenyl)ethylene are then hydrogenated in the presence of a hydrogenation catalyst, thereby obtaining another aimed product of the present invention, 1,2-di(4-isobutylphenyl)ethane. This hydrogenation can be carried out by the conventional method. It should be noted, however, that the hydrogenation of aromatic rings should be avoided. The catalysts are exemplified by noble metal catalysts such as palladium and platinum, other metallic catalysts such as nickel, cobalt and molybdenum, or carrier-supported catalysts in which the above catalysts are carried on a suitable carrier such as carbon. The reaction temperature is in the range of room temperature to 100° C. and the pressure is atmospheric pressure to 50 kg/cm$^2$. After the reaction, the aimed compound of 1,2-di(4-isobutylphenyl)ethane can be obtained by separating it through an appropriate means such as distillation.

In the following, methods for preparing 4-isobutylstyrene using the foregoing two kinds of intermediate compounds are described. In one method, 1,2-di(4-isobutylphenyl)ethylene is disproportionated with ethylene to produce 4-isobutylstyrene. In the other method, 1,2-di(4-isobutylphenyl)ethane is catalytically cracked in the presence of an acid catalyst to obtain 4-isobutylstyrene.

In the first place, the method with disproportionation is described.

The obtained 1,2-di(4-isobutylphenyl)ethylene and ethylene are reacted in the presence of a disproportionation metal catalyst containing a metal such as rhenium, molybdenum or tungsten to obtain 4-isobutylstyrene without difficulty. For the disproportionation according to the present invention, any of trans-1,2-di(4-isobutylphenyl)ethylene and cis-1,2-di(4-isobutylphenyl)ethylene can be used, which reaction is called also as metathesis.

The catalysts for this disproportionation are oxides or sulfides of metals such as rhenium, molybdenum and tungsten, or their mixtures. They can be used either singly or in combination with a promoter or a third additive of a metal such as rhodium, vanadium, aluminum, titanium, manganese, niobium, iridium, tellurium and alkali metals or a mixture with the oxides or sulfides of them, or an organometal of aluminum or tin such as alkylaluminum, or hydrogen, carbon monoxide, or ammonia.

These catalysts can be also used in the form in which it is supported on a proper carrier. For example, the carriers of $TiO_2$, $ThO_2$, $MgO_2$, $ZrO_2$, $TaO_2$, $Nb_2O_5$ and $SnO_2$, and phosphates of Al, Mg, Ca, Zr and Ta as well as silica, alumina and silica-alumina, are used.

Exemplified as the main catalysts used for disproportionation are $ReO_3$, $MoO_2$, $MoS_3$, $WS_2$ and $Re_2S_7$ as well as $WO_3$, $MoO_3$ and the $Re_2O_7$.

The disproportionation catalyst can be prepared by the conventional method. For example, an oxide carrier is impregnated with an aqueous solution of a metal salt and it is then baked. Used also in the disproportionation of the present invention are those prepared by appropriately fixing the foregoing carbonyl complex or alkyl complex to an oxide carrier and then baking it.

The type of reaction to be employed is not especially limited and any of gaseous phase and liquid phase reaction can be adopted. The reaction temperature is usually selected from the range of 0° C. to 700° C., especially depending upon the kind of catalyst used. For example, when a catalyst exhibiting high activity in lower temperatures is used such as in the case of rhenium oxide, the reaction temperature of 0° C. to 100° C., preferably 5° C. to 90° C., is sufficient. In the cases of other catalysts of lower activity, they may be used in the temperature range of 200° C. to 700° C., preferably 300° C. to 600° C. When the disproportionation is carried out at lower temperatures, the side reactions such as isomerization and polymerization hardly occur. Accordingly, taking together the economy into consideration, it is desirable that the reaction is carried out at a temperature lower than 100° C. using a highly active disproportionation catalyst such as a rhenium catalyst. Incidentally, as the reaction is done with introducing ethylene, it is carried out under a raised pressure of 1 to 100 kg/cm², however, a pressure of 1 to 10 kg/cm² is generally sufficient.

In addition, the coexistence of inert gases such as helium or nitrogen or hydrocarbons of benzene or hexane that are inert to the disproportionation does not cause any hindrance in the reaction.

The molar ratio between ethylene and 1,2-di(4-isobutylphenyl)ethylene can be arbitrarily selected. In general, however, a ratio in the range between 1:10 to 10:1, preferably 1:5 to 5:1, may be selected. The type of reaction may be any of continuous and batch wise. In the continuous type, the SV (space velocity) may be selected from the range of 0.01 to 1000, preferably 0.1 to 100.

After the disproportionation, 4-isobutylstyrene can be obtained by separating it by an appropriate separation means such as reduced-pressure distillation.

The method for producing 4-isobutylstyrene through the catalytic cracking of 1,2-di(4-isobutylphenyl)ethane will be described.

In this step, 1,2-di(4-isobutylphenyl)ethane is brought into contact with an acid catalyst such as a solid acid catalyst, preferably in a diluted state with the coexistence of an inert gas. As the inert gas, any of inorganic gases such as hydrogen, helium, argon, nitrogen and steam and, in addition, those which do not hinder the activity of acid catalyst such as methane, ethane and propane, can be used. The inert gases can be used singly or in a mixture of them. In view of the handling in industrial practice, steam is a preferable one. The dilution with an inert gas, the molar ratio as represented by [inert gas]/[1,2-di(4-isobutylphenyl)ethane] is preferably not less than 50. The upper ratio is not especially limited and the higher the better, however, the molar ratio of 500 is an upper limit in view of industrial practice.

The solid acid catalysts to be brought into contact are synthetic solid acid catalysts such as silica-alumina, silica-magnesia and zeolite, natural solid acid substances such as activated clay, acid clay, kaolin and attapulgite, and solid catalysts carrying protonic acid such as inorganic porous carrier with no acidic activity such as silica or alumina that is impregnated with a protonic acid. The protonic acids to impregnate are inorganic protonic acids such as phosphoric acid, sulfuric acid, hydrochloric acid and heteropoly-acids such as silicotungstic acid and phosphotungstic acid, and organic protonic acids such as benzenesulfonic acid and toluenesulfonic acid.

The temperature of contact with the solid acid catalyst is preferably in the range of 300° to 700° C., preferably 400° to 600° C. in view of the efficiency of reaction and the selectivity of cracking. The contact temperature below 300° C. is not desirable practically because the efficiency of reaction is low. On the other hand, the temperature above 700° C. is not desirable either because the loss of aimed product increases due to thermal polymerization.

The process in gas phase contact can be carried out in any of atmospheric, raised and reduced pressures as far as the diluted 1,2-di(4-isobutylphenyl)ethane is maintained in a gaseous phase. Furthermore, the type of reaction may be any of fixed bed, moving bed and fluidized bed.

The catalytic cracking reaction of the present invention is represented by the following chemical formulae:

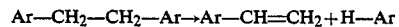

wherein Ar is a residual group of p-(iso-$C_4H_9$)-$C_6H_4\ominus$.

Being different from the case of the cracking of 1,1-di(4-isobutylphenyl)ethane, the fraction containing unreacted 1,2-di(4-isobutylphenyl)ethane does not contain substituted ethylene components which are formed by concomitant dehydrogenation. This unreacted component can be used again for the cracking just like the starting 1,2-di(4-isobutylphenyl)ethane used for this cracking.

The products of the catalytic reaction can be easily separated by conventionally known physical and chemical means. As physical means, for example, separation by solvent extraction utilizing the solubility to a solvent or the difference in distribution coefficients; separation by adsorption utilizing the difference in liability to be adsorbed; separation by crystallization utilizing the difference in melting points or freezing points; and separation by distillation utilizing the difference in boiling points.

Among the above separation means, the separation by distillation is preferable in a practical viewpoint owing to its easiness in operation. The isobutylbenzene, 4-isobutylstyrene and 1,2-di(4-isobutylphenyl)ethane contained in the reaction mixture of the method of the invention, can be easily separated by the conventional distillation method.

After the first step to produce 4-isobutylstyrene (hereinafter sometimes referred to as "PBS") from the above-described intermediate compounds of the present invention, in the next second step, α-(4-isobutylphenyl)-propionic acid (ibuprofen, hereinafter sometimes referred to as "IPA") or its lower alkyl ester (hereinafter sometimes referred to as "IPE") is produced by carbonylating PBS with carbon monoxide and water or lower alcohol (hydroesterification). In this second step, when PBS is carbonylated using carbon monoxide and hydrogen (hydroformylation), α-(4-isobutylphenyl)propionaldehyde (hereinafter sometimes referred to as "IPN") is produced. IPA can be easily produced by oxidizing this IPN through a conventional method.

The carbonylation will be described below.

In the step (II) as the second stage according to the the present invention, the carbonylation of PBS that is obtained in the preceding step (I) is done to obtain IPA or IPE, its ester of IPA.

This step can be carried out in accordance with the conventional method in which olefinic unsaturated compound is reacted with alcohol or water and carbon monoxide in the presence of a metal complex carbonylation catalyst.

When water is used, IPA is obtained, and when an alcohol is used, a corresponding ester of IPA is produced. The metal complex carbonylation catalysts are exemplified by metal complexes of precious metals such as Pd, Rh, Ir, Pt and Ru; and Ni, Co and Fe. With regard to the oxidation number of precious metals, any metals of zero to a maximum in oxidation number can be used and metal complexes having ligands of halogen atoms, trivalent phosphorus compounds, π-allyl groups, amines, nitriles, oximes, olefins and carbon monoxide are effective.

The metal complex carbonylation catalysts are exemplified by bistriphenylphosphine dichlorocomplex, bistributylphosphine dichlorocomplex, bistricyclohexylphosphine dichlorocomplex, π-allyltriphenylphosphine dichlorocomplex, triphenylphosphine piperidine dichlorocomplex, bisbenzonitrile dichlorocomplex, biscyclohexyloxime dichlorocomplex, 1,5,9-cyclododecatriene dichlorocomplex, bistriphenylphosphine dicarbonyl complex, bistriphenylphosphine diacetate complex, bistriphenylphosphine dinitrate complex, bistriphenylphosphine sulfate complex, tetrakistriphenylphosphine complex; and complexes in which a part of ligands are carbon monoxide such as chlorocarbonyl bistriphenylphosphine complex, hydridocarbonyl tristriphenylphosphine, bischlorotetracarbonyl complex and dicarbonyl acetylacetonate complex, of the above-mentioned metals.

Furthermore, compounds which produces the above metal complexes in the reaction system can be also used. That is, phosphine, nitrile, allyl compound, amine, oxime, olefin or carbon monoxide which is able to be the ligands to the oxides, sulfates or chlorides of the above precious metals or else, are simultaneously added into the reaction system in the carbonylation reaction.

The above phosphines are exemplified by triphenylphosphine, tritolylphosphine, tributylphosphine, tircyclohexylphosphine and triethylphosphine. The nitriles are exemplified by benzonitrile, acrylonitrile, propionitrile and benzylnitrile. The allyl compounds are exemplified by allyl chloride and allyl alcohol. The amines are exemplified by benzylamine, pyridine, piperazine and tri-n-butylamine. The oximes are exemplified by cyclohexyloxime, acetoxime and benzaldoxime. The olefins are exemplified by 1,5-cyclooctadiene and 1,5,9-cyclododecatriene.

The alcohols used in this step are lower aliphatic alcohols having 1 to 4 carbon atoms such as methanol, ethanol, propanol and butanol. When higher alcohols than the above ones are used, the boiling point of produced IPE is too high, which is undesirable because the refining of IPE is difficult.

The quantity of a metal complex or a compound which produces a metal complex to be used in this step as a catalyst is 0.0001 to 0.5 mole, preferably 0.001 to 0.1 mole to one mole of PBS. When the compound which produces a metal complex is used, the addition quantity of the compound to form ligands is 0.8 to 10 moles, preferably 1 to 4 moles to one mole of the compound to produce a metal complex.

Alcohol and water act as solvents as well as reactants. The use quantities of them are 0.5 to 50 parts by weight, preferably 1 to 20 parts by weight, to one part by weight of PBS.

Furthermore, for the purpose of improving the rate of reaction, it is possible to add inorganic halides such as hydrogen chloride and boron trifluoride, or organic iodide such as methyl iodide.

When these halides are added, the quantities of them are 0.1 to 30 moles, preferably 1 to 15 moles, as halogen atoms to 1 mole of the complex catalyst or the compound to produce a complex. Even though it depends upon the kind of catalyst, if the addition quantity is less than 0.1 mole, the effect of the addition cannot be produced sometimes. If the addition quantity exceeds 30 times by moles, not only the catalytic activity is lowered but also halogen atoms are added to the double bonds of PBS which fact becomes a bar to the aimed reaction.

It is only necessary that the quantity of carbon monoxide to be fed is excess relative to the quantity of PBS. Even though it depends upon the size and form of a reaction vessel, the termination of reaction can be confirmed generally by observing the phenomenon that the absorption of carbon monoxide that exists in the reaction vessel under pressure is ceased and the lowering of the pressure within the reaction vessel is also ceased.

The carbonylation reaction is carried out at temperatures in the range of 40° to 150° C., preferably 60° to 110° C., and at a carbon monoxide pressure in the range of 5 to 500 kg/cm², preferably 30 to 400 kg/cm². If the reaction temperature is below 40° C., the rate of reaction is very low which is not acceptable in industrial practice. On the other hand, if the reaction temperature is above 150° C., it is not desirable because side reactions of polymerization and decomposition of complex catalyst are caused to occur. Also, if the pressure of carbon monoxide is lower than 5 kg/cm², the reaction rate is so slow that the reaction cannot be carried out practically. The upper limit of the pressure is not limited but in a practical viewpoint, it is desirable that the pressure is not higher than 500 kg/cm². It is sufficient that the reaction is continued until the lowering of pressure owing to the absorption of carbon monoxide is stopped. When the carbonylation is carried out using water as a solvent, the IPA is produced. While, by using an alcohol as a solvent, an alkyl ester of IPA, i.e. IPE which has the ester moiety of the alkyl group of the alcohol, can be easily obtained. Because the IPE obtained in the presence of alcoholic solvent is stable, the IPE can be refined easily by simple distillation or the like. Furthermore, the final product of α-(p-isobutylphenyl)propionic acid can be easily obtained by the convention method of hydrolysis of esters. For example, the IPE is refluxed with an aqueous solution of sodium hydroxide and the precipitate of the acid, IPA, is separated and recrystallized in n-hexane or petroleum ether. The thus obtained α-(p-isobutylphenyl)propionic acid is very pure.

It is possible to use again the metal complex catalyst that is recovered after the reaction.

In place of the foregoing step (II), a step (III) can be carried out as a second stage. In the step (III), PBS is reacted with hydrogen and carbon monoxide in the presence of a metal complex carbonylation catalyst to obtain IPN and it is then oxidized to produce IPA.

The kinds, quantities and manner of use of the metal complex carbonylation catalysts will not be described here repeatedly because they are just the same as those in the foregoing step (II). Furthermore, it is also the same that inorganic halides and organic iodides can be added in order to improve the rate of reaction.

The carbonylation reaction in the step (III) is carried out at temperatures in the range of 40° C. to 150° C., preferably 55° C. to 110° C. If the reaction temperature is below 40° C., the rate of reaction is very low which is not acceptable in industrial production process. On the other hand, if the reaction temperature is above 150° C., it is not desirable because side reactions of polymerization and addition of hydrogen, and decomposition of complex catalyst are caused to occur.

The pressure of reaction may be properly determined as far as it is above 5 kg/cm². If the reaction pressure is lower than 5 kg/cm², the rate of reaction is so low that the reaction cannot be carried out practically. If the reaction pressure is high enough, the reaction will proceed faster, however, a too high pressure requires highly pressure resistant reaction apparatus, which will determined the upper limit of reaction pressure. It is thus practically sufficient that the reaction pressure is set on a level lower than 500 kg/cm².

The reaction is continued until the lowering of pressure owing to the absorption of the mixed gas of carbon monoxide and hydrogen, is ceased. The reaction time of 4 to 20 hours is generally sufficient.

The carbon monoxide and hydrogen which are used in the reaction can be fed either separately or by mixing them previously. The molar ratio of carbon monoxide and hydrogen to be fed into the reaction system can be selected arbitrary. In this carbonylation reaction of step (III) of the invention, carbon monoxide and hydrogen are consumed (absorbed) accurately at a molar ratio of 1:1. Accordingly, as the gas supplied in excess remains unreacted, the reaction is made to proceed again if the other gas is supplied at the time when the lowering of pressure is ceased and reactants still remain. Even though it will depend upon the size of reaction vessel and the mode of reaction, it is generally most effective that carbon monoxide and hydrogen are fed in a molar ratio of 1:1.

In the carbonylation in this step of the invention, it is possible to use a solvent which is inert to the carbonylation in order to remove the heat of reaction. Exemplified as the solvents that are inert to carbonylation are polar solvents such as ethers, ketones and alcohols, and nonpolar solvents such as paraffins, cycloparaffins and aromatic hydrocarbons. However, satisfactory result can also be obtained generally in the condition without any solvent.

The thus obtained reaction product is then distilled under a reduced pressure to separate IPN and the catalyst quite easily. The recovered complex catalyst can be used again for the next carbonylation reaction.

In this step of the invention, the carbonylation is carried out by using the stable and highly pure PBS that is obtained in the step (I). Accordingly, the obtained IPN contains only a small quantity of β-(p-isobutylphenyl)propionaldehyde (NPN) and it can be easily refined to produce highly pure IPN.

Because IPN can be prepared in a very pure form by the method of the invention, α-(p-isobutylphenyl)propionic acid (IPA) can be easily obtained by oxidizing IPN.

The oxidation is carried out under relatively moderate conditions because IPN has an aldehyde group and a hydrogen atom on α-position. For example, IPN is oxidized by a mild oxidizing agent of an aqueous solution of potassium permanganate, an aqueous alkaline suspension of silver oxide, or bromine water. Especially preferable oxidizing method is to oxidize with a hypohalogenous acid under an acidic condition. The hypohalogenous acid are exemplified by sodium, potassium and calcium salts of hypochlorous acid or hypobromous acid. It is desirable that the oxidation is performed with cooling at temperatures in the range of −10° C. to 30° C.

The highly pure PBS obtained in the preceeding step is then carbonylated in the succeeding step to produce IPA, IPE or IPN. In the carbonylation of PBS, highly pure products scarcely containing impurities can be obtained. The IPE obtained with the solvent of alcohol can be easily hydrolyzed into IPA, meanwhile, the IPA is directly produced when water is used as a solvent. The IPN is also easily converted into IPA by oxidation.

In other words, the method for producing IPA or its ester of IPE has been accomplished by turning attention to the new compounds and by using more inexpensive materials as compared with those in the conventional method and by employing a simple and easily handled intermediate compound of the present invention. Therefore, the method of the present invention can be said to be epochal.

In the following, the present invention will be described in more detail with reference to several examples.

EXAMPLE 1

Synthesis of Di(4-isobutylphenyl)iodonium Salt

A mixture of 107 g of potassium periodate, 134 g of isobutylbenzene and 400 ml of acetic anhydride was fed into a three-neck flask having a cooling tube and the contents were stirred at 5° C. to 10° C. A mixture of 204 g of acetic anhydride and 196 g of concentrated sulfuric acid was added dropwise little by little to the above mixture over two hours. The temperature of reaction was maintained at 5° to 10° C. After the temperature of the reaction mixture was restored to room temperature, the stirring was continued for further 16 hours.

This reaction mixture was poured into ice water of 600 ml. By adding then a saturated aqueous solution of 100 g of potassium bromide, diisobutylphenyl iodonium salt was crystallized out. Water was separated from this crystal by reduced-pressure filtration and the crystal was further washed with water and subjected to reduced-pressure filtration, again. This was dried in vacuum at 50° C. to obtain 167 g of di(4-isobutylphenyl)iodonium bromide (melting point: 180° to 182° C.).

EXAMPLE 2

Reaction of Ethylene with Di(4-isobutylphenyl)iodonium Salt

A mixture of 94.6 g of di(4-isobutylphenyl)iodonium bromide, 37 g of tri-n-butylamine, 2 g of palladium acetate and 500 ml of methanol was fed into 1 liter flask equipped with a reflux condenser and a stirrer. Then, with supplying 100 ml/min of ethylene gas, the contents were stirred at 50° C. for 16 hours.

After the reaction, methanol was evaporated off under reduced pressure. After 1 liter of water was added to this solution, extraction with toluene was carried out. The toluene layer was dried with magnesium sulfate and then filtered. After that, toluene was evaporated under reduced pressure. The remained liquid was subjected to recrystallization using methanol as a solvent to obtain 25 g of crystal having a melting point of 106° to 108° C.

The purity of this crystal was 98.0% and it was conformed by IR analysis and NMR analysis that the crystal was p-diisobutylstilbene [1,2-di(4-isobutylphenyl)ethylene].

| Elemental Analysis: (as $C_{22}H_{28}$) | | | | |
|---|---|---|---|---|
| C: 90.45% | | (calc'd 90.35%) | | |
| H: 9.55% | | (calc'd 9.65%) | | |
| IR: (KBr method, cm$^{-1}$) | | | | |
| 810, | 850, | 970, | 1370, | 1390, |
| 1470, | 1610, | 1910, | 2970, | 3030 |
| NMR ($^1$H-NMR, δ) | | | | |
| 0.9 | Doublet | (12 H) | | |
| 1.8–2.0 | Multiplet | (2 H) | | |
| 2.5 | Doublet | (4 H) | | |
| 7.0 | Singlet | (2 H) | | |
| 7.0–7.5 | Multiplet | (8 H) | | |

EXAMPLE 3

Preparation of 1,2-isobutylphenyl)ethane by Hydrogenation

To a 1 liter autoclave were fed 5 g of 1,2-di(4-isobutylphenyl)ethylene, 200 ml of diethyl ether and 0.5 g of Pd-carbon catalyst (5% Pd, made by Nippon Engelhard, Ltd.). The pressure was then raised to 10 kg/cm$^2$ by supplying pure hydrogen. Stirring was continued for 16 hours under the same pressure. After the reaction, unreacted hydrogen gas was exhausted to restore it to atmospheric pressure. The catalyst was then filtered off to obtain an ether solution. The ether was removed by evaporation and 4.8 g of crystal was obtained. The crystal was further subjected to recrystallization with methanol, thereby obtaining 4.3 g flaky crystal of 1,2-di(4-isobutylphenyl)ethane with supplying 100 ml/min of ethylene gas, the contents were stirred at 50° C. for 16 hours.

In the following, the results of analysis of this product are shown.

| Melting Point: 29 to 31° C. | | | | |
|---|---|---|---|---|
| Elemental Analysis: (as $C_{22}H_{30}$) | | | | |
| C: 89.71% | | (calc'd 89.73%) | | |
| H: 10.29% | | (calc'd 10.27%) | | |
| IR: (KBr method, cm$^{-1}$) | | | | |
| 795, | 840, | 1020, | 1110, | 1170, |
| 1370, | 1390, | 1470, | 1510, | 1620, |
| 1680, | 1790, | 1900, | 2970, | 3030 |
| NMR ($^1$H-NMR, δ) | | | | |
| 0.8–1.0 | Doublet | (12 H) | | |
| 1.8–2.0 | Multiplet | (2 H) | | |
| 2.4–2.6 | Doublet | (4 H) | | |
| 2.9 | Singlet | (4 H) | | |
| 7.0–7.3 | Multiplet | (8 H) | | |

EXAMPLE 4

Disproportionation with Rhenium Catalyst

γ-Alumina (100 g) was impregnated with an aqueous solution of 26.3 g of rhenium heptoxide for 24 hours. It was then dried at 120° C. and baked at 600° C. for 5 hours. A reaction tube was filled with 20 ml of the thus prepared catalyst together with a filler of α-alumina. Before reaction, activation was done by heating it in a nitrogen atmosphere under a pressure of 1 kg/cm$^2$ at 590° C. for 2 hours.

After cooling it to room temperature, a 1:3 mixture of 1,2-di(4-isobutylphenyl)ethylene and benzene, and ethylene were fed to the reaction tube. The molar ratio of 1,2-di(4-isobutylphenyl)ethylene to ethylene was 1 to 1.2 and SV (hr$^{-1}$) was 6. After allowing it to react for 3 hours at 30° C., the reaction liquid was subjected to gas chromatographic analysis and it was understood that 4-isobutylstyrene was obtained in a conversion rate of 60% on 1,2-di(4-isobutylphenyl)ethylene.

EXAMPLE 5

Disproportionation with Tungsten Catalyst

Ammonium paratungstate (5 g) was dissolved in 200 ml of water and 100 g of silica gel was put into this solution with stirring. It was then dried at 120° C. and baked in the air at 600° C. for 5 hours. A reaction tube was filled with 20 ml of the thus prepared catalyst together with a filler of α-alumina. Before reaction, activation was done by heating it in a nitrogen atmosphere under a pressure of 1 kg/cm$^2$ at 590° C. for 2 hours.

Reaction was carried out at 400° C. The molar ratio of 1,2-di(4-isobutylphenyl)ethylene to ethylene was 1 to 1.2 and GHSV (gas hourly space velocity) was 60. After allowing it to react for 3 hours, the reaction liquid was subjected to gas chromatographic analysis and it was understood that 4-isobutylstyrene was obtained in a conversion rate of 40% on 1,2-di(4-isobutylphenyl)ethylene.

EXAMPLE 6

Disproportionation with Another Catalyst

Activated alumina was impregnated with ammonium molybdate and it was dried at 120° C. and then baked in the air at 600° C. for 5 hours. This catalyst consisted of Mo$_3$ and Al$_2$O$_3$ and the atomic ratio (Mo/Al) thereof was 1/25. A reaction tube was filled with 20 ml of the thus prepared catalyst together with a filler of α-alumina. Before reaction, activation was carried out by heating it in a nitrogen atmosphere under a pressure of 1 kg/cm² at 590° C. for 2 hours.

Using this catalyst, reaction was carried out in the like manner as in Example 4 to obtain 4-isobutylstyrene in a conversion rate of 30% on 1,2-di(4-isobutylphenyl)ethylene.

EXAMPLE 7

Disproportionation of 1,2-di(4-isobutylphenyl)ethylene with ethylene was carried out using the same catalyst and reaction apparatus as those in Example 5. The reaction temperature was 400° C., the molar ratio of 1,2-di(4-isobutylphenyl)ethylene to ethylene was 1 to 1.2, and GHSV was 60. After 3 hours' reaction, the reaction liquid was subjected to gas chromatographic analysis and it was understood that 4-isobutylstyrene was obtained in a conversion rate of 30% on 1,2-di(4-isobutylphenyl)ethylene.

EXAMPLE 8

Cracking of 1,2-Di(4-isobutylphenyl)ethane

A silica-alumina catalyst (trademark: N-631-L, made by Nikki Chemical Corp.) of 15 to 25 mesh was prepared. It was fed as deep as 135 mm into a reaction tube of 12 mm in inner diameter made of stainless steel. This was heated to 500° C. by an electric furnace and cracking was carried out by continuously feeding 15 ml/hr of 1,2-di(4-isobutylphenyl)ethane and 150 ml/hr of water. After cooling the outlet of the reaction tube, the oily layer was separated from 6 hours to 54 hours after the start of reaction and it was subjected to gas chromatographic analysis. The results are shown in the following Table 1.

TABLE 1

| Results of Gas Chromatographic Analysis | |
|---|---|
| Fraction | Weight (%) |
| Lighter fraction | 0.6 |
| Isobutylbenzene fraction | 13.3 |
| 4-Isobutylethylbenzene fraction | 1.8 |
| 4-Isobutylstyrene fraction | 11.3 |
| Unreacted 1,2-di(4-isobutylphenyl)ethane fraction | 72.3 |
| Heavier fraction | 0.7 |

The product of cracking was subjected to precision fractional distillation to obtain a 4-isobutylstyrene fraction (recovery rate: 88%) in a distillation temperature range of 74° C. to 89° C. and under a reduced pressure of 30 to 34 mmHg and a recovered fraction of unreacted 1,2-diphenylethane (recovery rate: 92%) in a distillation temperature range of 178° to 185° C. under a reduced pressure of 2 to 3 mmHg.

The bromine number of 1,2-(4-isobutylphenyl)ethane fraction, corresponding to the recovered unreacted fraction, was 0.20. According to mass spectrometry, the content of component of m/e=292 was 0.3% (m/e of 1,1-di(4-isobutylphenyl)ethane is 294).

COMPARATIVE EXAMPLE 1

Cracking of 1,1-Di(4-isobutylphenyl)ethane

4-Isobutylbenzene and acetaldehyde were reacted in the presence of sulfuric acid catalyst. In connection with 1,1-di(4-isobutylphenyl)ethane (bromine number: 0.16) of 177° to 184° C. in distillation temperature at 2 to 3 mmHg, cracking was carried out in the like manner as in Example 8.

It was subjected to gas chromatographic analysis, the results of which are shown in the following Table 2.

TABLE 2

| Results of Gas Chromatographic Analysis | |
|---|---|
| Fraction | Weight (%) |
| Lighter fraction | 2.7 |
| Isobutylbenzene fraction | 24.6 |
| 4-Isobutylethylbenzene fraction | 2.3 |
| 4-Isobutylstyrene fraction | 24.8 |
| Unreacted 1,1-di(4-isobutylphenyl)ethane fraction | 44.3 |
| Heavier fraction | 1.3 |

The product of cracking was subjected to precision fractional distillation to obtain a 4-isobutylstyrene fraction (recovery rate: 73%) and a recovered fraction of unreacted 1,1-di(4-isobutylphenyl)ethane (recovery rate: 91%) in a distillation temperature range of 175° to 185° C. under a reduced pressure of 2 to 3 mmHg.

The bromine number of the recovered 1,1-di(4-isobutylphenyl)ethane fraction was 3.5. According to mass spectrometry, the content of component of m/e=292 was 6.0% (m/e of 1,1-di(4-isobutylphenyl)ethane is 294).

EXAMPLE 9

Re-Cracking of Recovered Fraction

The diarylethane fractions corresponding to the fractions of unreacted materials which were recovered in Example 8 and Comparative Example 1 were cracked intact in the like manner as in Example 8 to compare the changes in the ratios of cracking with the passage of time in the cracking reaction.

The results are shown in the following Table 3.

TABLE 3

| Fraction | Changes in Ratios of Cracking with the Passage of Time[*1] | | | | Content[*2] |
|---|---|---|---|---|---|
| | 12 hr | 24 hr | 48 hr | 72 hr | |
| Example 8 | 0.88 | 0.67 | 0.54 | 0.53 | 0.3 |
| Comp. Ex. 1 | 0.83 | 0.51 | 0.39 | 0.31 | 8.2 |

Notes:
[*1] Values relative to the ratio of cracking as 1.00 at 6 hours after the start of reaction.
[*2] The content of substituted ethylene component in a diphenylethane fraction. In mass spectrometry, the intensity of substituted ethylene component of (m/e) - 2 is indicated provided that the intensity of m/e of diphenylethane is 100.

As will be understood from the above results, the change in the ratio of catalytic cracking with the passage of time in Example 8 is smaller as compared with that of Comparative Example 1.

EXAMPLE 10

Using catalysts shown in the following Table 4, 1,2-di(4-isobutylphenyl)ethane was cracked in the like manner as in Example 8. The results of them are shown also in Table 4.

TABLE 4

| Experiment Number | Catalyst | Ratio of Cracking (%) | Content of Substituted Ethylene Component (wt. %) |
|---|---|---|---|
| | Clay-type solid catalyst | | |
| 10-1 | Kaolin clay | 32 | 0.3 |
| 10-2 | Attapulgus clay (made by | 26 | 0.2 |

TABLE 4-continued

| Experiment Number | Catalyst | Ratio of Cracking (%) | Content of Substituted Ethylene Component (wt. %) |
|---|---|---|---|
| | Nippon Engelhard, Ltd) Synthetic silica-alumina solid catalyst | | |
| 10-3 | FCC-HA (trademark, made by Catalyst & Chem. Ind. Co.) Zeolite-type solid catalyst | 31 | 0.2 |
| 10-4 | MR-Z (trademark, made by Catalyst & Chem. Ind. Co.) | 33 | 0.3 |

EXAMPLE 11

Preparation of IPA or IPE by Carbonylation of PBS

To a 500 ml autoclave with a stirrer were fed 30 g of PBS obtained in Example 8, 100 ml of ethyl alcohol, 1 g of bistriphenylphosphine dichloropalladium and 0.2 g of 30% boron trifluoride solution in ethyl ether. It was pressurized to 80 kg/cm$^2$ with carbon monoxide and reaction was carried out until the absorption of carbon monoxide was ceased.

After the reaction, the autoclave was cooled and unreacted gas was exhausted. By adding 1 g of potassium carbonate powder to the contents, a fraction of 90°-115° C./1 mmHg was obtained by simple distillation under reduced pressure, thereby separating the catalyst. According to the gas chromatographic analysis of this fraction, the composition thereof was 1.0 wt. % PBE(isobutylethylbenzene), 0.3 wt. % PBS, 93.6 wt. % IPE (ethyl ester) and 0.6 wt. % of ethyl ester of β-(p-isobutylphenyl)propionic acid (5 components).

The above fraction was distilled again under a reduced pressure to obtain 38 g of IPE (ethyl ester) of 119° C. to 121° C./1 mmHg. The purity of the product was 99.7% according to gas chromatographic analysis. Furthermore, the chemical structure of the product was confirmed by comparing with an authentic sample by IR analysis.

EXAMPLE 12

To a 500 ml autoclave were fed 30 g of PBS obtained in Example 8, 150 ml of 5% hydrogen chloride solution in methyl alcohol and 1 g of bisdichlorotriphenylphosphine palladium. It was pressurized to 350 kg/cm$^2$ at room temperature with carbon monoxide and, after heating to 95° C., it was pressurized further to 700 kg/cm$^2$ with carbon monoxide. The reaction was continued until the absorption of carbon monoxide was ceased.

After the reaction, the reaction product was treated in the like manner as Example 11 to obtain 21 g of IPE (ethyl ester) of the boiling point of 119° C. to 121° C./1 mmHg.

EXAMPLE 13

To a 500 ml autoclave were fed 30 g of PBS obtained in Example 8, 75 g of 10% hydrochloric acid aqueous solution, 0.8 g of bisdichlorotriphenylphosphine palladium, 80 ml of benzene as a reaction solvent and 1 g of acetophenone. It was pressurized to 100 kg/cm$^2$ with carbon monoxide at room temperature. After heating it to 100° C., it was further pressurized to 300 kg/cm$^2$ with carbon monoxide and reaction was continued until the absorption of carbon monoxide was ceased.

After the reaction, the autoclave was cooled and benzene layer was separated and it was extracted three times with 50 ml of 5% aqueous solution of sodium hydroxide. Then hydrochloric acid was added until the sodium hydroxide solution became pH 2 and extracted with chloroform. The chloroform was removed by reduced pressure evaporation to obtain 36 g of light yellow crude crystal. This crude crystal was recrystallized with n-heptane to obtain a white crystal of IPA having a melting point of 75.5° to 76.5° C. The recovery ratio by recrystallization was 81%. The maximum absorption of the ethanol solution of the white crystal in ultraviolet absorption was 220 mμ and, besides it, light absorption at 257 mμ, 263 mμ and 272 mμ was observed. Furthermore, it was confirmed by IR analysis that the obtained crystal was the same as the authentic sample.

EXAMPLE 14

Using 0.37 g of palladium chloride and 0.63 g of triphenylphosphine in place of the bisphenylphosphine dichloropalladium, reaction was carried out in the like manner as Example 11 and results similar to those of Example 11 were obtained.

EXAMPLE 15

Using 0.7 g of palladium dibenzylideneacetone and 1.2 g of diphenetyl neopentylphosphine in place of the bisphenylphosphine dichloropalladium, and 3 ml of trifluoroacetic acid in place of boron trifluoride ethyl ether solution, reaction was carried out in the like manner as Example 11 and 29 g of IPE (ethyl ester) of 99.4% purity was obtained.

REFERENCE EXAMPLE

Hydrolysis of Ethyl Ester

A mixture of 10g of IPE (ethyl ester) obtained in Example 11 and 200 ml of 12% sodium hydroxide aqueous solution was prepared and hydrolysis of IPE was carried out at the refluxing temperature for 3 hours.

After cooling, oily content was extracted with ethyl ether and rinsed with water, and hydrochloric acid was added until the aqueous layer became pH 2. It was then extracted with carbon tetrachloride and the carbon tetrachloride was removed under a reduce pressure to obtain 8.1 g of light yellow crude crystal. The crude crystal was recrystallized with n-heptane to obtain 6.7 g of white crystal having a melting point of 75° C. to 76° C.

This crystal as compared with the authentic sample and as a result, it was understood that the crystal was the same IPA as that of Example 13.

EXAMPLE 16

Preparation of α-(p-Isobutylphenyl)propionaldehyde (IPN) from p-Isobutylstyrene (PBS)

To a 500 ml autoclave with a stirrer were fed 30 g of PBS obtained in Example 4 and 0.4 g of rhodium hydridocarbonyl tristriphenylphosphine. It was heated to 70° C. and pressurized to 50 kg/cm$^2$ with an equimolar gas mixture of hydrogen and carbon monoxide. The reaction was continued until the absorption of the mixed gas was ceased. After the reaction, the autoclave was cooled and the remaining mixed gas was exhausted. The contents were transferred into a simple distillation still and 33 g of crude IPN fraction of a distilling range of 65° to 91° C./2 mmHg was obtained. The composition of the obtained fraction is shown in the following Table 5.

TABLE 5

| Composition of Crude IPN Fraction | |
|---|---|
| Component | Content (wt. %) |
| PBE | 0.2 |
| PBS | 0.1 |
| IPN | 90.8 |
| NPN | 8.9 |

This crude IPN fraction was treated again by reduced pressure distillation to obtain 25 g of IPN of a boiling range of 71° C. to 75° C./3 mmHg. The purity of this IPN was 99.7%.

Oxidation

A flask with a thermometer, a condenser, a dropping funnel and a stirrer was fed with 19.03 g of IPN obtained in the above process, 100 ml of acetone and 10.0 g of acetic acid. The reaction was carried out by adding 68.8 g of sodium hypochlorite (11% aqueous solution) dropwise for 2 hours with cooling and stirring maintaining the temperature in the range of −5° C. to −10° C. After the addition, the stirring was continued for further 1 hour.

The reaction mixture was then rinsed with water and extracted with benzene. The benzene layer was rinsed with water and neutralized with an aqueous solution of sodium hydroxide. It was then acidified by hydrochloric acid with cooling and it was further cooled to precipitate crystal. After recrystallization, IPA was obtained in a yield of 84%. The chemical structure of this was confirmed by comparing with an authentic sample.

EXAMPLE 17

Using 0.2 g of rhodium oxide and 1.5 g of triphenylphosphine in place of rhodium hydridocarbonyl tristriphenylphosphine, reaction was carried out in the like manner as Example 16. As a result, 30 g of crude IPN fraction containing 0.3 wt. % of PBE, 0.2 wt. % of PBS, 82.2 wt. % of IPN and 17.6 wt. % of NPN was obtained.

This crude IPN fraction was then oxidized in the like manner as Example 16 and IPA was obtained.

EXAMPLES 18 and 19

Hydroformylation

In place of rhodium hydridocarbonyl tristriphenylphosphine, the complex catalysts shown in the following Table 6 was used and reaction was carried out in the like manner as Example 16 at a reaction temperature of 95° C. and a reaction pressure of 170 kg/cm$^2$.

The results are shown in the following Table 6.

TABLE 6

| Example Number | Catalyst | Crude IPN Fraction (g) | GCL composition (wt. %) | | | |
|---|---|---|---|---|---|---|
| | | | PBE | PBS | IPN | NPN |
| 18 | IrCl(CO)(PPh$_3$)$_3$ | 23 | 3.3 | 0.8 | 76.2 | 19.7 |
| 19 | RuCl$_2$(PPh$_3$)$_2$ | 25 | 4.3 | 0.5 | 77.8 | 17.4 |

Note: "Ph" represents a "phenyl group"

What is claimed is:

1. 1,2-di(4-isobutylphenyl)hydrocarbon which is represented by the following formula (I):

$$\begin{array}{c} H_3C \\ \phantom{H_3C}\diagdown \\ \phantom{H_3CC}CH-CH_2-\phenyl-R-\phenyl-CH_2-CH \\ \phantom{H_3C}\diagup \\ H_3C \end{array} \begin{array}{c} CH_3 \\ \diagup \\ \\ \diagdown \\ CH_3 \end{array} \quad (I)$$

wherein the substituent R represents either
  a substituent —CH$_2$—CH$_2$— or
  a substituent —CH=CH—.

2. The compound according to claim 1 wherein R is —CH$_2$—CH$_2$—.

3. The compound according to claim 1 wherein R is —CH=CH—.

4. The compound according to claim 3, wherein the compound is trans-1,2-di(4-isobutylphenyl)ethylene.

5. The compound according to claim 3, wherein the compound is cis-1,2-di(4-isobutylphenyl)ethylene.

* * * * *

UNITED STATES PATENT AND TRADEMARK OFFICE
CERTIFICATE OF CORRECTION

PATENT NO. : 4,885,419

DATED : December 5, 1989

INVENTOR(S) : Isoo Shimizu, et al.

It is certified that error appears in the above-identified patent and that said Letters Patent is hereby corrected as shown below:

```
Column 5, line 27:  delete "the"
Column 16, line 51:  "as"  should read as
--was--
```

Signed and Sealed this

Thirteenth Day of August, 1991

Attest:

HARRY F. MANBECK, JR.

Attesting Officer

Commissioner of Patents and Trademarks